United States Patent
Aladahalli et al.

(10) Patent No.: US 11,903,760 B2
(45) Date of Patent: Feb. 20, 2024

(54) SYSTEMS AND METHODS FOR SCAN PLANE PREDICTION IN ULTRASOUND IMAGES

(71) Applicant: GE Precision Healthcare LLC, Milwaukee, WI (US)

(72) Inventors: Chandan Kumar Aladahalli, Karnataka (IN); Krishna Seetharam Shriram, Karnataka (IN); Vikram Melapudi, Karnataka (IN)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 176 days.

(21) Appl. No.: 17/447,094

(22) Filed: Sep. 8, 2021

(65) Prior Publication Data
US 2023/0075063 A1  Mar. 9, 2023

(51) Int. Cl.
*A61B 8/00* (2006.01)
*A61B 8/08* (2006.01)

(52) U.S. Cl.
CPC .......... *A61B 8/4254* (2013.01); *A61B 8/463* (2013.01); *A61B 8/5207* (2013.01)

(58) Field of Classification Search
None
See application file for complete search history.

(56) References Cited

U.S. PATENT DOCUMENTS

| | | | |
|---|---|---|---|
| 10,825,188 B1 * | 11/2020 | Tan | G06T 7/11 |
| 10,878,529 B2 * | 12/2020 | Sloan | G16H 50/20 |
| 11,454,976 B1 * | 9/2022 | Levinson | G05D 1/0221 |

(Continued)

FOREIGN PATENT DOCUMENTS

| | | | | |
|---|---|---|---|---|
| DE | 112021002345 T5 * | 4/2023 | | A61B 8/461 |
| EP | 4109463 A1 * | 12/2022 | | G16H 15/00 |

(Continued)

OTHER PUBLICATIONS

Bahner, D. et al., "Language of Transducer Manipulation: Codifying Terms for Effective Teaching," Journal of Ultrasound Medicine, vol. 35, No. 1, Jan. 2016, Available Online Dec. 17, 2015, 7 pages.

(Continued)

*Primary Examiner* — Mohammed Rachedine
(74) *Attorney, Agent, or Firm* — McCoy Russell LLP

(57) ABSTRACT

The current disclosure provides systems and methods for providing guidance information to an operator of a medical imaging device. In an embodiment, a method is provided, comprising training a deep learning neural network on training pairs including a first medical image of an anatomical neighborhood and a second medical image of the anatomical neighborhood as input data, and a ground truth displacement between a first scan plane of the first medical image and a second scan plane of the second medical image as target data; using the neural network to predict a displacement between a first scan plane of a new medical image of the anatomical neighborhood and a target scan plane of a reference medical image of the anatomical neighborhood; and displaying guidance information for an imaging device used to acquire the new medical image on a display screen.

20 Claims, 7 Drawing Sheets

(56) References Cited

U.S. PATENT DOCUMENTS

| | | | |
|---|---|---|---|
| 11,779,309 B2* | 10/2023 | Pourtahmasi Roshandeh | G01S 7/52025 600/437 |
| 11,798,180 B2* | 10/2023 | Yin | G06T 7/50 |
| 2016/0143627 A1 | 5/2016 | Vignon et al. | |
| 2018/0153505 A1 | 6/2018 | Cadieu et al. | |
| 2019/0108634 A1* | 4/2019 | Zaharchuk | G06T 3/60 |
| 2023/0043026 A1* | 2/2023 | Duan | G06V 10/22 |
| 2023/0285774 A1* | 9/2023 | Chen | G16H 20/40 600/1 |

FOREIGN PATENT DOCUMENTS

| | | | | |
|---|---|---|---|---|
| JP | 7325954 B2 * | 8/2023 | | G06N 3/0454 |
| WO | WO-2020219757 A1 * | 10/2020 | | A61B 6/03 |

OTHER PUBLICATIONS

Yen-Chen, L. et al., "iNeRF: Inverting Neural Radiance Fields for Pose Estimation," arXiv Cornell University Website, Available Online at https://arxiv.org/abs/2012.05877, Available as Early as Dec. 10, 2020, 9 pages.

* cited by examiner

SYSTEMS AND METHODS FOR SCAN PLANE PREDICTION IN ULTRASOUND IMAGES

TECHNICAL FIELD

Embodiments of the subject matter disclosed herein relate to ultrasound imaging, and more particularly, to systems and methods for probe guidance during ultrasound examinations.

BACKGROUND

Clinical ultrasound is an imaging modality that employs ultrasound waves to probe the internal structures of a body of a patient and produce a corresponding image. An ultrasound probe comprising a plurality of transducer elements emits ultrasonic pulses which reflect or echo, refract, or are absorbed by structures in the body. The ultrasound probe then receives reflected echoes, which are processed into an image. For example, a medical imaging device such as an ultrasound imaging device may be used to obtain images of a heart, uterus, liver, lungs, and various other anatomical regions of a patient.

As an operator manipulates an ultrasound probe of an imaging system, the imaging system may provide guidance to the operator, including using artificial intelligence (AI) techniques to assist the operator in acquiring high-quality ultrasound images. The guidance may include providing annotations on a display device of the imaging system and/or providing indications to the operator to adjust the ultrasound probe. For example, the imaging system may instruct the operator to move the ultrasound probe in a direction, to rotate the ultrasound probe in a rotational direction, adjust a pressure placed on the ultrasound probe, and/or perform a different adjustment of the ultrasound probe.

Probe movement guidance in ultrasound may rely on an estimation of a current scan plane of the probe with respect to a target scan plane. However, current AI methods to assess scan planes for quality, guidance, etc. are specific to a target scan plane, and hence they are not easily adaptable to a newly chosen target scan plane. As a result, developing a robust scan plane assessment system may entail training multiple models, long training and/or development times, and elaborate and bespoke annotations. Other alternative approaches may require expensive sensory data collection (e.g., via an electromagnetic (EM) tracker) or registration with three-dimensional (3-D) anatomical references.

SUMMARY

The current disclosure at least partially addresses one or more of the above identified issues by a method comprising, training a deep learning (DL) neural network on training pairs including a first medical image of an anatomical neighborhood and a second medical image of the anatomical neighborhood as input data, and a ground truth displacement between a first scan plane of the first medical image and a second scan plane of the second medical image as target data; using the trained DL neural network to predict a displacement between a first scan plane of a new medical image of the anatomical neighborhood and a target scan plane of a reference medical image of the anatomical neighborhood; and displaying guidance information for an imaging device used to acquire the new medical image on a display screen of the image processing system based on the predicted displacement and/or storing the guidance information for further processing. In some embodiments, the guidance information may include probe guidance cues that aid an operator in acquiring images of a higher quality in real time. In other embodiments, the guidance information may include an assessment of a quality of one or more acquired images, or explain an assessment or quality score assigned to the operator. For example, the predicted displacement may be used to characterize and/or assess one or more actions previously performed by the operator by comparing successive frames in a video recording. By training the DL neural network using pairs of images from an anatomical neighborhood as input data and a ground truth predicted displacement as target data, a general-purpose model may be created that may predict a relative displacement between scan planes of arbitrarily chosen source and target images acquired in the anatomical neighborhood. In this way, a general purpose probe guidance system may be advantageously created at a lower cost than guidance systems that rely on feature detection and/or costly sensors.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

Figure 1:
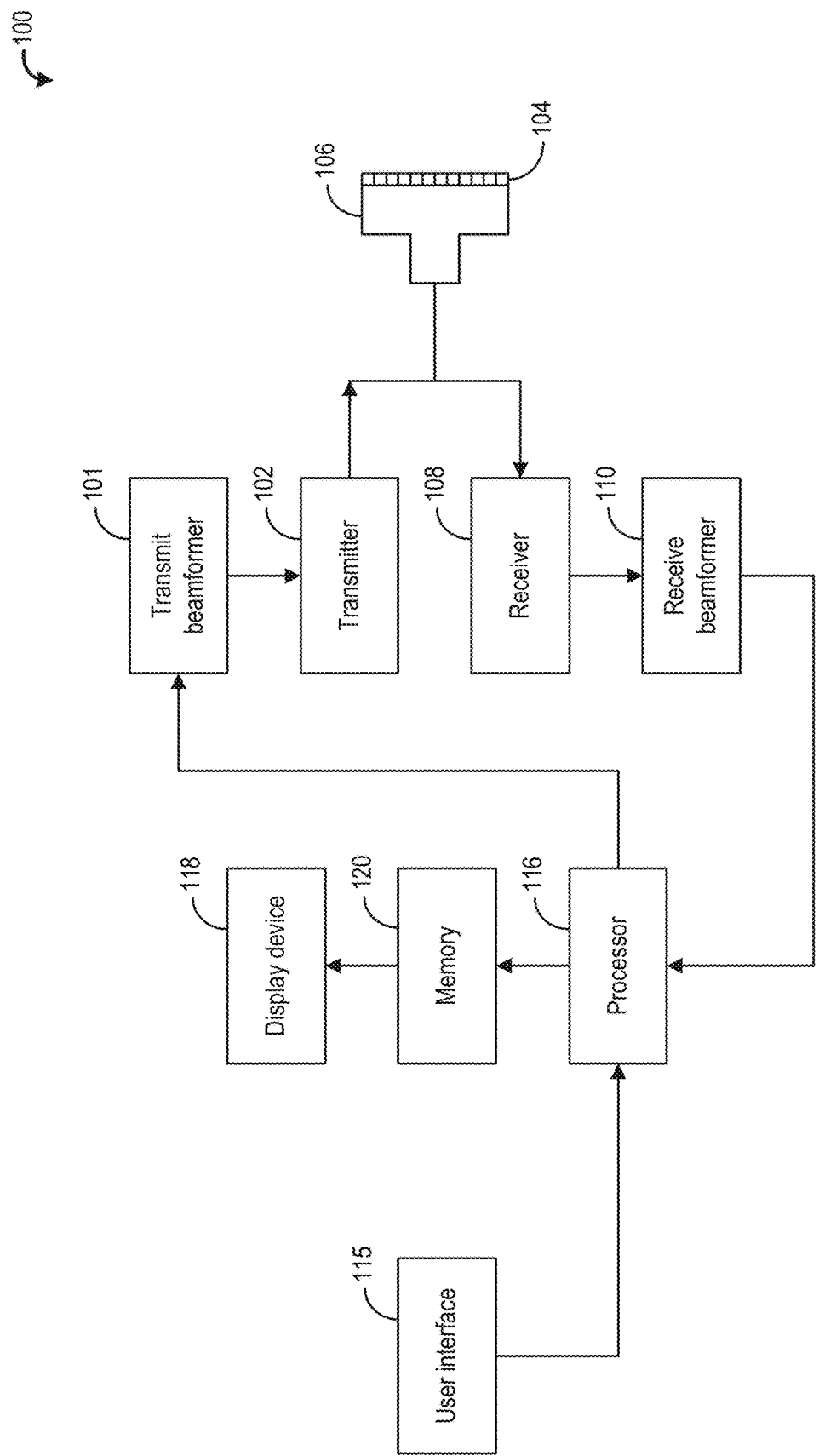
FIG. 1 shows a block diagram of an exemplary embodiment of an ultrasound system.

The drawings illustrate specific aspects of the described systems and methods for mapping one or more ultrasound images in a first resolution to one or more corresponding ultrasound images in a target resolution using generative neural networks. Together with the following description, the drawings demonstrate and explain the structures, methods, and principles described herein. In the drawings, the size of components may be exaggerated or otherwise modified for clarity. Well-known structures, materials, or operations are not shown or described in detail to avoid obscuring aspects of the described components, systems, and methods.

DETAILED DESCRIPTION

Clinical ultrasound imaging typically includes the placement of an ultrasound probe including one or more transducer elements onto an imaging subject, such as a patient, at the location of a target anatomical feature (e.g., abdomen, chest, etc.). Images are acquired by the ultrasound probe and are displayed on a display device in real time or near real time (e.g., the images are displayed once the images are generated and without intentional delay). The operator of the ultrasound probe may view the images and adjust various acquisition parameters and/or the position, pressure, and/or orientation of the ultrasound probe in order to obtain high-quality images of the target anatomical feature (e.g., the heart, the liver, the kidney, or another anatomical feature). Obtaining the high-quality images may include adjusting the ultrasound probe to attain a desired or target scan plane, wherein the target anatomical feature is visible with a high degree of clarity and completeness. A scan plane is a two-dimensional plane corresponding to a two-dimensional image of a scanned feature generated during a scan. Attaining the desired or target scan plane may lead to a better patient experience, a more accurate diagnosis, and/or improved clinical outcomes.

During a training of the operator, various approaches may be used to provide probe movement guidance to the operator in real time during an examination to aid the operator in attaining the desired or target scan plane. The probe movement guidance may rely on an estimation of a difference or deviation between a current probe placement and an ideal probe placement. In some approaches, an absolute difference (e.g., as opposed to a relative distance) may be estimated using sensors. For example, the absolute difference may be estimated using an inertial measurement unit (IMU), including an accelerometer, a gyroscope, and a magnetometer. However, due to a high cost of the sensors, a cost of implementing an IMU-based approach may be high, which may negatively impact a scalability of the IMU-based approach.

Other AI-based approaches include training a neural network to learn a relative difference between an image acquired by an operator based on a current probe placement and a target image based on an ideal probe placement. However, such approaches may rely on detecting a selected anatomical feature present in both the image and the target image. For example, various approaches may entail registration of a selected anatomical feature with an anatomical reference, or training a machine learning (ML) model using a target image of the selected anatomical feature. However, because such approaches may be specific to the selected anatomical feature, developing an image processing system with robust probe guidance capabilities may include developing a plurality of different models for different anatomical regions, sub-regions, features, or perspectives. Because training each different model may entail collecting different training data, a cost of developing the image processing system may be high, and therefore a scalability of the AI-based approaches may be negatively impacted.

As an alternative, the present disclosure provides systems and methods for developing a generic deep learning (DL) neural network model for predicting a displacement between a first scan plane at which a first image of an anatomical neighborhood is acquired, and a second scan plane at which a second image of the anatomical neighborhood is acquired. Guidance information may then be provided to an operator of an ultrasound probe (or a different handheld imaging device) based on the predicted displacement. The predicted displacement may comprise, for example, a direction of movement and/or a change in an orientation of the handheld imaging device to achieve the second (e.g., target) scan plane from the first (e.g., current) scan plane.

In some embodiments, the guidance information may comprise probe movement guidance cues and/or information displayed on a display screen coupled to the handheld imaging device in real time. In other embodiments, the guidance information may comprise an analysis and/or quality assessment of a series of movements of the ultrasound probe performed by the operator at a prior time. For example, relative scan plane displacements between image frames in a sequence of ultrasound images and a target scan plane may be used to generate an assessment of how efficiently the operator manipulated an ultrasound probe to acquire an ultrasound image at the target scan plane.

Because the guidance information is based on a predicted displacement between two scan planes of an anatomical neighborhood, and not based on a presence of a specific anatomical feature, the generic deep learning (DL) neural network may be trained on a single set of image data of the anatomical neighborhood, and subsequently used to generate the guidance information for any target scan plane of the anatomical neighborhood. Thus, the present disclosure may represent a lower cost and more scalable alternative to other approaches to probe guidance. Another advantage of the systems and methods disclosed herein is that guidance information provided based on scan plane displacement may not constrain the operator to a sequence of movements to acquire a target scan plane, but may rather indicate a general direction, leaving the operator responsible for choosing a path to the target scan plane.

It should be appreciated that while the disclosed systems and methods are described herein in reference to an ultrasound imaging system, the disclosed systems and methods may also be used in conjunction with other types of medical imaging systems in which an operator manually manipulates a probe to acquire a desired medical image.

In various embodiments, one or more ultrasound images are acquired via an ultrasound probe of an ultrasound imaging system, such as the ultrasound imaging system 100 of FIG. 1. The ultrasound imaging system may be communicatively coupled to an image processing system, such as image processing system 202 of FIG. 2. The image processing system may include one or more neural network models stored in non-transitory memory. An exemplary neural network algorithm may be trained using a scan plane displacement prediction network training system 300, shown in FIG. 3, to output a relative displacement between a first scan plane and a second scan plane within an anatomical neighborhood of a subject. Example scan planes within an anatomical neighborhood of a subject are shown in FIGS. 4A, 4B, 4C, 4D, and 4E. A training set used to train the scan plane displacement prediction network may be generated by following one or more steps of method 500 of FIG. 5. Probe guidance cues may be generated on a display screen of a handheld imaging device including a probe based on an output of the scan plane displacement prediction network, by following one or more steps of method 600 of FIG. 6. A performance of an operator of the handheld imaging device may be assessed based on the output of the scan plane displacement prediction network by following one or more steps of method 700 of FIG. 7.

Referring now to FIG. 1, a schematic diagram of an ultrasound imaging system 100 in accordance with an embodiment of the disclosure is shown. The ultrasound imaging system 100 includes a transmit beamformer 101 and a transmitter 102 that drives elements (e.g., transducer elements) 104 within a transducer array, herein referred to as probe 106, to emit pulsed ultrasonic signals (referred to herein as transmit pulses) into a body (not shown). The probe 106 may be a one-dimensional transducer array probe, or the probe 106 may be a two-dimensional matrix transducer array probe. As explained further below, the transducer elements 104 may be comprised of a piezoelectric material. When a voltage is applied to a piezoelectric crystal, the crystal physically expands and contracts, emitting an ultrasonic spherical wave. In this way, transducer elements 104 may convert electronic transmit signals into acoustic transmit beams.

After the elements 104 of the probe 106 emit pulsed ultrasonic signals into a body (of a patient), the pulsed ultrasonic signals are back-scattered from structures within an interior of the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. Additionally, transducer element 104 may produce one or more ultrasonic pulses to form one or more transmit beams in accordance with the received echoes.

According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system. In one embodiment, data acquired via ultrasound system 100 may be used to train a machine learning model. A user interface 115 may be used to control operation of the ultrasound imaging system 100, including to control the input of patient data (e.g., patient clinical history), to change a scanning or display parameter, to initiate a probe repolarization sequence, and the like. The user interface 115 may include one or more of the following: a rotary element, a mouse, a keyboard, a trackball, hard keys linked to specific actions, soft keys that may be configured to control different functions, and/or a graphical user interface displayed on a display device 118.

The ultrasound imaging system 100 also includes a processor 116 to control the transmit beamformer 101, the transmitter 102, the receiver 108, and the receive beamformer 110. The processer 116 is in electronic communication (e.g., communicatively connected) with the probe 106. For purposes of this disclosure, the term "electronic communication" may be defined to include both wired and wireless communications.

The processor 116 may control the probe 106 to acquire data according to instructions stored on a memory of the processor, and/or memory 120. The processor 116 may control which of the elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processor (CPU), according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment, the demodulation can be carried out earlier in the processing chain.

The processor 116 is adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay. For example, an embodiment may acquire images at a real-time frame-rate of 7-20 frames/sec. The ultrasound imaging system 100 may acquire 2D data of one or more planes at a significantly faster rate. However, it should be understood that the real-time frame-rate may be dependent on a length of time that it takes to acquire each frame of data for display. Accordingly, when acquiring a relatively large amount of data, the real-time frame-rate may be slower. Thus, some embodiments may have real-time frame-rates that are considerably faster than 20 frames/sec while other embodiments may have real-time frame-rates slower than 7 frames/sec.

The data may be stored temporarily in a buffer (not shown) during a scanning session and processed in less than real-time in a live or off-line operation. In some embodiments, multiple processors (not shown) may be included to handle the processing tasks that are handled by processor 116 according to the exemplary embodiment described hereinabove. For example, a first processor may be utilized to demodulate and decimate the RF signal while a second processor may be used to further process the data, for example by augmenting the data as described further herein, prior to displaying an image. It should be appreciated that other embodiments may use a different arrangement of processors.

The ultrasound imaging system 100 may continuously acquire data at a frame-rate of, for example, 10 Hz to 30 Hz (e.g., 10 to 30 frames per second). Images generated from the data may be refreshed at a similar frame-rate on display device 118. Other embodiments may acquire and display data at different rates. For example, some embodiments may acquire data at a frame-rate of less than 10 Hz or greater than 30 Hz depending on the size of the frame and the intended application. A memory 120 is included for storing processed frames of acquired data. In an exemplary embodiment, the memory 120 is of sufficient capacity to store at least several seconds' worth of frames of ultrasound data. The frames of data are stored in a manner to facilitate retrieval thereof according to its order or time of acquisition. The memory 120 may comprise any known data storage medium.

In various embodiments of the present invention, data may be processed in different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. As one example, the one or more modules may process color Doppler data, which may include traditional color flow Doppler, power Doppler, HD flow, and the like. The image lines and/or frames are stored in memory and may include timing information indicating a time at which the image lines and/or frames were stored in memory. The modules may include, for example, a scan conversion module to perform scan conversion operations to convert the acquired images from beam space coordinates to display space coordinates. A video processor module may be provided that reads the acquired images from a memory and displays an image in real time while a procedure (e.g., ultrasound imaging) is being performed on a patient. The video processor module may include a separate image memory, and the ultrasound images may be written to the image memory in order to be read and displayed by display device 118.

In various embodiments of the present disclosure, one or more components of ultrasound imaging system 100 may be included in a portable, handheld ultrasound imaging device. For example, display device 118 and user interface 115 may be integrated into an exterior surface of the handheld ultrasound imaging device, which may further contain processor 116 and memory 120. Probe 106 may comprise a handheld probe in electronic communication with the handheld ultrasound imaging device to collect raw ultrasound data. Transmit beamformer 101, transmitter 102, receiver 108, and receive beamformer 110 may be included in the same or different portions of the ultrasound imaging system 100. For example, transmit beamformer 101, transmitter 102, receiver 108, and receive beamformer 110 may be included in the handheld ultrasound imaging device, the probe, and combinations thereof.

After performing an ultrasound scan, a two-dimensional block of data comprising scan lines and their samples is generated for each row of transducers comprised by the ultrasound probe (e.g., one block of data for a 1D probe, or n blocks of data for a 2D probe with n rows of transducers). After back-end filters are applied, a process known as scan conversion is performed to transform the two-dimensional data block into a displayable bitmap image with additional scan information such as depths, angles of each scan line, and so on. During scan conversion, an interpolation technique is applied to fill missing holes (e.g., pixels) in the resulting image. These missing pixels occur because each element of the two-dimensional block should typically cover many pixels in the resulting image. For example, in current ultrasound imaging systems, a bicubic interpolation is applied which leverages neighboring elements of the two-dimensional block. As a result, if the two-dimensional block is relatively small in comparison to the size of the bitmap image, the scan-converted image will include areas of poor or low resolution, especially for areas of greater depth.

Ultrasound images acquired by ultrasound imaging system 100 may be further processed. In some embodiments, as described in greater detail below, ultrasound images produced by ultrasound imaging system 100 may be transmitted to an image processing system, where the ultrasound images may be analyzed by one or more machine learning (ML) models. For example, an ML model may be trained using ultrasound images and corresponding ground truth images or data to increase a quality of the ultrasound images, to provide quality assessments of acquired images, and/or to generate guidance cues to aid an operator in adjusting a position, pressure, or rotation of the probe 106. As used herein, ground truth output refers to an expected or "correct" output based on a given input into a machine learning model. For example, if a machine learning model is being trained to detect a displacement between a scan plane of an input image and a scan plane of a target image, the ground truth output for the model, when fed an input image, may be an estimated displacement including a direction of the displacement (e.g., superior, inferior, rotation, etc.).

Although described herein as separate systems, it will be appreciated that in some embodiments, ultrasound imaging system 100 includes an image processing system. In other embodiments, ultrasound imaging system 100 and the image processing system may comprise separate devices. In some embodiments, images produced by ultrasound imaging system 100 may be used as a training data set for training one or more machine learning models, wherein the machine learning models may be used to perform one or more steps of ultrasound image processing, as described below.

Figure 2:
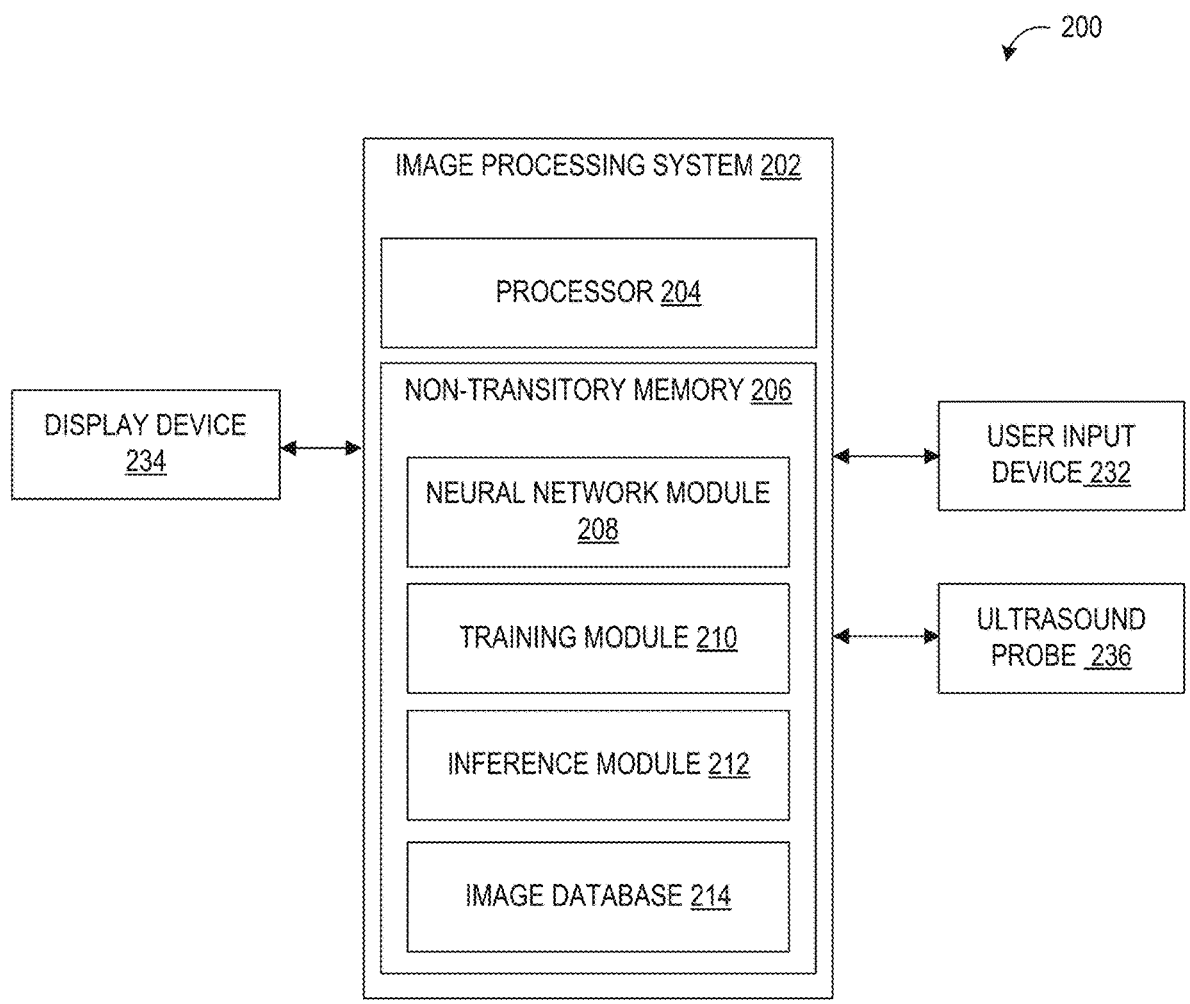
FIG. 2 shows a block diagram of an exemplary embodiment of an image processing system.

Referring to FIG. 2, a block diagram 200 shows an image processing system 202, in accordance with an embodiment. In some embodiments, image processing system 202 is incorporated into the ultrasound imaging system 100. For example, image processing system 202 may be provided in the ultrasound imaging system 100 as the processor 116 and memory 120. In some embodiments, at least a portion of image processing 202 is disposed at a device (e.g., edge device, server, etc.) communicably coupled to the ultrasound imaging system via wired and/or wireless connections. In some embodiments, at least a portion of image processing system 202 is disposed at a separate device (e.g., a workstation) which can receive images from the ultrasound imaging system or from a storage device which stores the images/data generated by the ultrasound imaging system. Image processing system 202 may be operably/communicatively coupled to a user input device 232 and a display device 234. User input device 232 may comprise the user interface 115 of the ultrasound imaging system 100, while display device 234 may comprise the display device 118 of the ultrasound imaging system 100, at least in some examples. Image processing system 202 may also be operably/communicatively coupled to an ultrasound probe 236.

Image processing system 202 includes a processor 204 configured to execute machine readable instructions stored in non-transitory memory 206. Processor 204 may be single core or multi-core, and the programs executed thereon may be configured for parallel or distributed processing. In some embodiments, processor 204 may optionally include individual components that are distributed throughout two or more devices, which may be remotely located and/or configured for coordinated processing. In some embodiments, one or more aspects of processor 204 may be virtualized and executed by remotely-accessible networked computing devices configured in a cloud computing configuration.

Non-transitory memory 206 may store a neural network module 208, a network training module 210, an inference module 212, and an image database 214. Neural network module 208 may include at least a deep learning model (e.g., a neural network), and instructions for implementing the deep learning model to predict a displacement of a scan plane of an ultrasound image from a target ultrasound scan plane, as described in greater detail below. Neural network module 208 may include trained and/or untrained neural networks and may further include various data, or metadata pertaining to the one or more neural networks stored therein.

Non-transitory memory 206 may further store a training module 210, which may comprise instructions for training one or more of the neural networks stored in neural network module 208. Training module 210 may include instructions that, when executed by processor 204, cause image processing system 202 to conduct one or more of the steps of method 500 for generating a training data set for training a neural network model, discussed in more detail below in reference to FIG. 5. In some embodiments, training module 210 may include instructions for implementing one or more gradient descent algorithms, applying one or more loss functions, and/or training routines, for use in adjusting parameters of one or more neural networks of neural network module 208. Training module 210 may include training datasets for the one or more neural networks of neural network module 208.

Non-transitory memory 206 also stores an inference module 212. Inference module 212 may include instructions for deploying a trained deep learning model, for example, to provide guidance cues to an operator of the ultrasound probe as described in FIG. 6, or to provide a quality assessment of one or more movements of the ultrasound probe made by the operator during an examination, as described in FIG. 7. In particular, inference module 212 may include instructions that, when executed by processor 204, cause image processing system 202 to conduct one or more of the steps of the methods 500, 600, and 700, as described in further detail below.

Non-transitory memory 206 further stores image database 214. Image database 214 may include for example, ultrasound images acquired via an ultrasound probe and images acquired via an ultrasound probe. For example, image database 214 may store images acquired via a handheld ultrasound probe placed on a body of a subject, and/or images acquired via an endoscopic ultrasound probe inserted into a cavity of the body of the subject. Image database 214 may include one or more training sets for training the one or more neural networks of neural network module 208.

In some embodiments, non-transitory memory 206 may include components disposed at two or more devices, which may be remotely located and/or configured for coordinated processing. In some embodiments, one or more aspects of non-transitory memory 206 may include remotely-accessible networked storage devices configured in a cloud computing configuration.

User input device 232 may comprise one or more of a touchscreen, a keyboard, a mouse, a trackpad, a motion sensing camera, or other device configured to enable a user to interact with and manipulate data within image processing system 202. In one example, user input device 232 may enable a user to make a selection of an image to use in training a machine learning model, or for further processing using a trained machine learning model.

Display device 234 may include one or more display devices utilizing virtually any type of technology. In some embodiments, display device 234 may comprise a computer monitor, and may display ultrasound images. Display device 234 may be combined with processor 204, non-transitory memory 206, and/or user input device 232 in a shared enclosure, or may be peripheral display devices and may comprise a monitor, touchscreen, projector, or other display device known in the art, which may enable a user to view ultrasound images produced by an ultrasound imaging system, and/or interact with various data stored in non-transitory memory 206.

It should be understood that image processing system 202 shown in FIG. 2 is for illustration, not for limitation. Another appropriate image processing system may include more, fewer, or different components.

Figure 3:
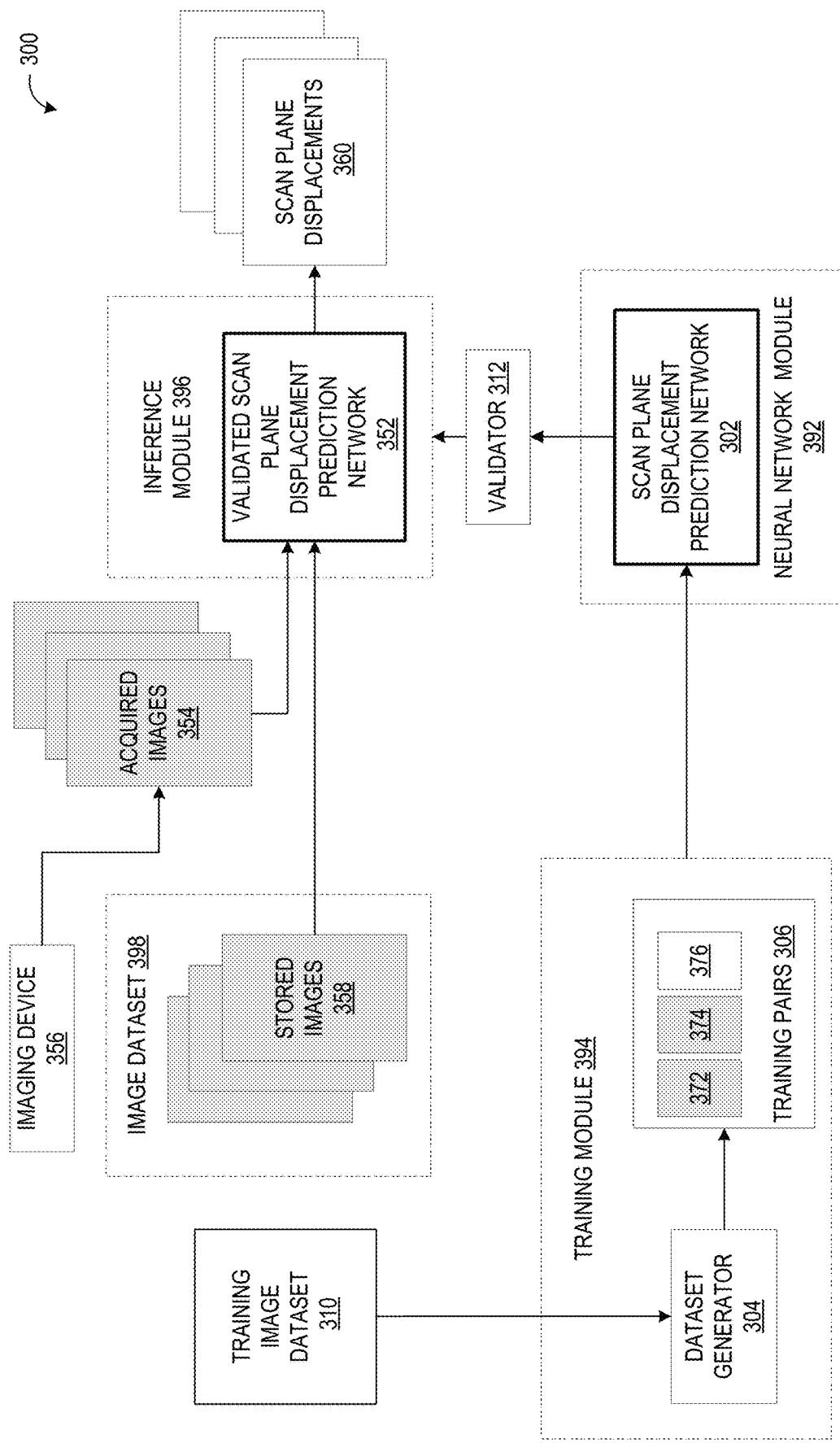
FIG. 3 shows a block diagram of an exemplary embodiment of a scan plane displacement prediction network training system.

Referring to FIG. 3, an example of a scan plane displacement prediction network training system 300 is shown. Scan plane displacement prediction network training system 300 may be implemented by one or more of an image processing system, such as image processing system 202 of FIG. 2, to train a DL neural network to predict a displacement between a first scan plane of an input image and a second scan plane of a target image. In an embodiment, scan plane displacement prediction network training system 300 includes a scan plane displacement prediction network 302, to be trained, which may be part of a neural network module 392 of the image processing system (e.g., neural network module 208 of FIG. 2).

The scan plane displacement prediction network may be trained on a training dataset, which may be stored in a training module 394 (e.g., training module 210 of FIG. 2). The training dataset may comprise a plurality of training pairs 306. Each training pair 306 may include input data, and ground truth target data.

In an embodiment, the input data may comprise an image pair including an input image 372 and a target image 374, where the input image 372 and the target image 374 are medical images acquired by an imaging device. For example, the medical images may be ultrasound images acquired via an ultrasound probe of an ultrasound imaging system (e.g., the ultrasound imaging system 100 of FIG. 1) during an examination of one or more anatomical structures of a patient. The input image 372 and the target image 374 of the image pair may be obtained from a training image dataset 310. Training image dataset 310 may be an image dataset of the image processing system generated from examinations performed on subjects, or training image dataset 310 may be an external image dataset such as a public dataset of medical images (e.g., Kaggle Breast Ultrasound Images (BUSI) Dataset, Kaggle Ultrasound Nerve Segmentation, etc.).

In various embodiments, the input image 372 and the target image 374 may be selected and paired by a dataset generator 304. Dataset generator 304 may generate image pairs by selecting a first image and a second image from a same anatomical neighborhood, and assigning the first image as the input image 372 and the second image as the target image 374. Alternatively, dataset generator 304 may assign the second image as the input image 372 and the first image as a target image 374. Additionally, each image pair of the training pairs may be assigned a ground truth target data 376. The ground truth target data 376 of the image pair may comprise a displacement between a scan plane of the input image 372 and a scan plane of the target image 374 of the image pair. For example, the displacement may be a direction and/or magnitude of a movement of a probe from a first estimated position at which the input image 372 was acquired, to a second estimated position at which an image substantially similar to the target image 374 may be acquired. Generation of the training pairs is described in greater detail below in reference to FIG. 5.

Once the training pairs 306 have been generated, the training pairs 306 may be assigned to either a training dataset or a test dataset. The test dataset may be used to prevent overfitting, whereby scan plane displacement prediction network 302 learns to map features specific to samples of the training set that are not present in the test set. As a non-limiting example, the number of training pairs 306 used may be 10,000, and the number of test pairs 308 used may be 1000.

In some embodiments, the training pairs 306 may be randomly assigned to either the training dataset or the test dataset in a pre-established proportion. For example, 90% of the training pairs 306 generated may be assigned to the training dataset, and 10% of the training pairs 306 generated may be assigned to the test dataset. In other embodiments, different proportions of training pairs 306 may be assigned to the training dataset and the test dataset. It should be appreciated that the examples provided herein are for illustrative purposes, and the training pairs 306 may be assigned to the training dataset or the test dataset via a different procedure and/or in a different proportion without departing from the scope of this disclosure.

Scan plane displacement prediction network training system 300 may be implemented to train scan plane displacement prediction network 302 to learn to predict the displacement between the scan plane of the input image 372 and the scan plane corresponding to the target image 374. Scan plane displacement prediction network 302 may be configured to receive the training pairs 306 from the training module 304, where the input image 372 and the corresponding target image 374 are inputted into scan plane displacement prediction network 302. Scan plane displacement prediction network 302 may output a predicted displacement between the scan plane of the input image 372 and the scan plane of the corresponding target image 374. Scan plane displacement prediction network 302 may then iteratively adjust one or more parameters of scan plane displacement prediction network 302 in order to minimize a loss function based on the predicted displacement, until an error rate decreases below a first threshold error rate.

Scan plane displacement prediction network training system 300 may include a validator 312 that validates a performance of scan plane displacement prediction network 302. Validator 312 may take as input a trained or partially trained scan plane displacement prediction network 302 and a test dataset of training pairs 306. If the error rate of the trained or partially trained scan plane displacement prediction network 302 on the test dataset of training pairs 306 decreases below a second threshold error rate, the performance of the trained or partially trained scan plane displacement prediction network 302 may be validated, whereby a training stage of the trained or partially trained scan plane displacement prediction network 302 may end.

For example, a partially trained scan plane displacement prediction network 302 of an image processing system may be validated with a test dataset of 50 training pairs 306, where each of the 50 training pairs 306 comprises an input image 372 of a spleen of a subject and a target image 374 of the spleen. The input image 372 may be acquired at a first scan plane, and the target image 374 may be acquired at a second, different scan plane. Validator 312 may feed the input image 372 and the target image 374 into the partially trained scan plane displacement prediction network 302 and receive a predicted displacement between the first scan plane and the second scan plane as an output. Validator 312 may then compare the predicted displacement with a (ground truth) displacement estimated by an expert. If an error between the predicted displacement and the ground truth target displacement is below the threshold error, the partially trained scan plane displacement prediction network 302 may be validated.

Scan plane displacement prediction network training system 300 may include an inference module 396, which comprises a validated scan plane displacement prediction network 352 that has been validated by validator 312 as described above. Inference module 396 may also include instructions for deploying validated scan plane displacement prediction network 352 to generate one or more predicted scan plane displacements 360 for one or more new input images.

In some embodiments, as described in greater detail below in reference to FIG. 6, the one or more new input images may include one or more acquired images 354, which may be acquired via a handheld imaging device 356 (such as an ultrasound probe) during an examination of a subject. The displacement predictions generated for the one or more acquired images 354 may be used, for example, to generate real-time guidance cues for a user of handheld imaging device 356.

In other embodiments, as described in greater detail below in reference to FIG. 7, the one or more new input images may include one or more stored images 358. The stored images 358 may include, for example, a sequence of image frames acquired at a previous time. The displacement predictions generated for the one or more stored images 358 may be used, for example, to generate an assessment of a performance of a user in achieving a desired scan plane. The stored images 354 may be accessed from an image dataset 398 of the image processing system. Image dataset 398 may be stored in an image database, such as image database 214 of FIG. 2.

Figure 5:
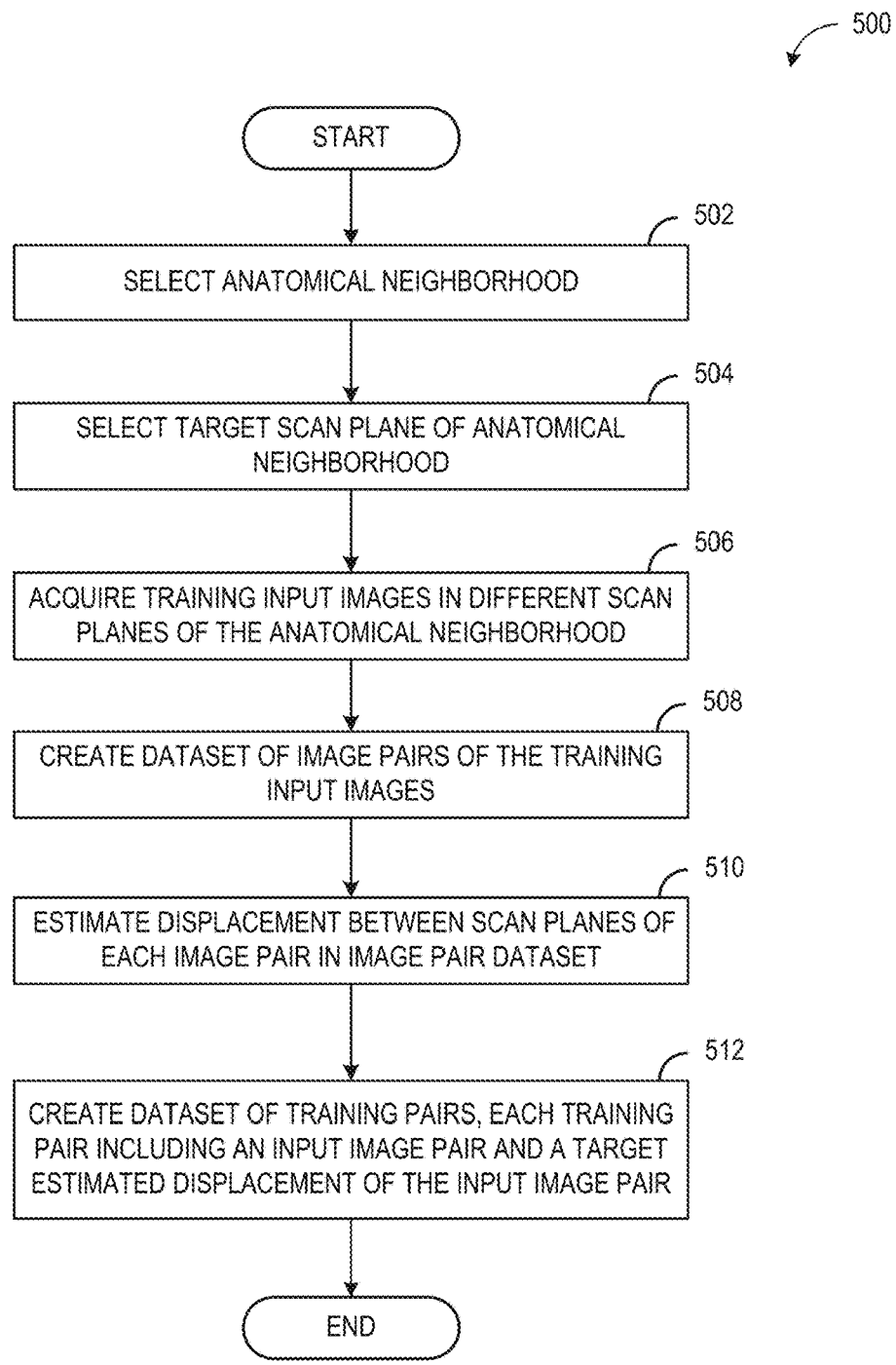
FIG. 5 is a flowchart illustrating an exemplary procedure for generating a training dataset for training the scan plane displacement prediction network.

Referring now to FIG. 5, an exemplary method 500 is shown for generating a training dataset for training a scan plane displacement prediction network (e.g., scan plane displacement prediction network 302) to predict a displacement between scan planes of an input image and a target image. The training dataset may comprise a plurality of training pairs, such as the training pairs 306 described above in reference to the scan plane displacement prediction network training system 300. Method 500 may be carried out by a dataset generator of a neural network training system, such as dataset generator 304 of the scan plane displacement prediction network training system 300. The neural network training system may be included in a module of an image processing system, such as image processing system 202, and one or more instructions of method 500 may be executed by a processor of the image processing system (e.g., processor 204).

It should be appreciated that in some embodiments, training the scan plane displacement prediction network may include generating a plurality of training datasets and training the scan plane displacement prediction network on each dataset of the plurality of training datasets. For example, the scan plane displacement prediction network may be trained on a first training dataset of a first anatomical neighborhood. After training has been completed on the first training dataset, the scan plane displacement prediction network may be trained on a second training dataset of a second anatomical neighborhood. After training has been completed on the second training dataset, the scan plane displacement prediction network may be trained on a third training dataset of a third anatomical neighborhood, and so on. After training the scan plane displacement prediction network on the plurality of training datasets corresponding to a plurality of anatomical neighborhoods, the scan plane displacement prediction network may predict a displacement between arbitrarily selected source and target scan planes of the plurality of anatomical neighborhoods.

Method 500 begins at 502, where method 500 includes selecting an anatomical neighborhood from which to collect sample images to be used in the training dataset. In some embodiments, the anatomical neighborhood may include a region of interest (ROI), such as an internal organ. For example, the anatomical neighborhood may be a right upper quadrant (RUQ) of an abdomen, and an ROI of the anatomical neighborhood may be a right kidney visible in the RUQ.

At 504, method 500 includes selecting one or more target scan planes of the anatomical neighborhood. Each target scan plane of the anatomical neighborhood may be a scan plane at which one or more features of the ROI are visible with a high degree of clarity and/or completeness. Different target scan planes of the anatomical neighborhood may allow different features of the ROI to be visible. For example, at a first target scan plane, a first set of features of the ROI may be visible with a high degree of clarity and/or completeness, and a second set of features of the ROI may not be visible with a high degree of clarity and/or completeness. At a second target scan plane, the first set of features of the ROI may not be visible with a high degree of clarity and/or completeness, and the second set of features of the ROI may be visible with a high degree of clarity and/or completeness. The target scan plane may represent a scan plane at which an optimal image may be acquired to view an abnormality (e.g., a lesion, a tumor, etc.) of the ROI. Thus, different target scan planes may be applicable to different subject-specific concerns and/or specific to a type of examination. To generate a suitable training dataset, a plurality of target scan planes may be selected for the anatomical neighborhood.

In various embodiments, a plurality of target scan planes may be pre-established by the image processing system. For example, the image processing system may include a library of target scan planes applicable to different types of examinations, and a target scan plane may be selected from the library of target scan planes. For example, if the anatomical neighborhood is the RUQ of the abdomen, and a right kidney is a ROI, a target scan plane may be a right kidney mid-transverse plane.

At 506, method 500 includes acquiring training input images in different scan planes of the anatomical neighborhood. The training input images may be images acquired at any scan plane of the anatomical neighborhood that is not the target scan plane. If the anatomical neighborhood includes an ROI, the training input images may be any images acquired at a scan plane that includes a cross section of the ROI. For example, if the anatomical neighborhood is the RUQ of the abdomen with the right kidney as a ROI, a training input image may be an image that includes a cross section of the right kidney. In other embodiments, the anatomical neighborhood may not include a specific ROI, or may include more than one ROI.

Figure 4A:
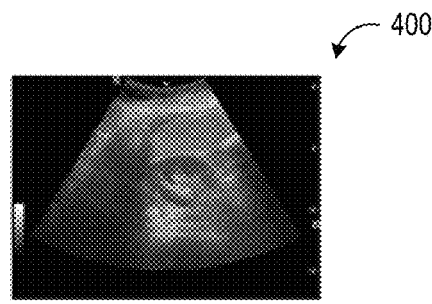
FIG. 4A is an example ultrasound image acquired in a first scan plane.
Figure 4B:
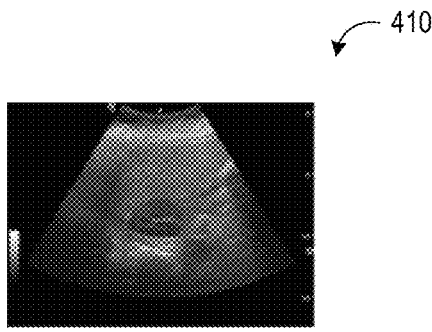
FIG. 4B is an example ultrasound image acquired in a second scan plane.
Figure 4C:
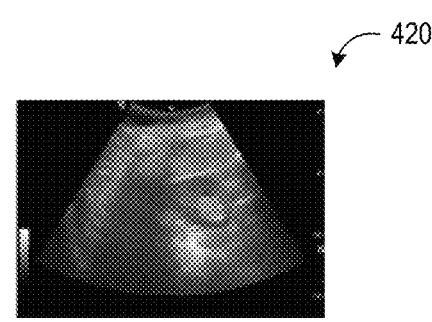
FIG. 4C is an example ultrasound image acquired in a third scan plane.
Figure 4D:
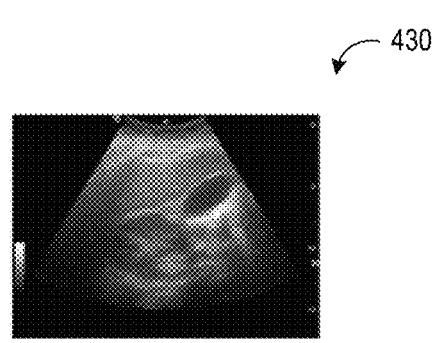
FIG. 4D is an example ultrasound image acquired in a fourth scan plane.
Figure 4E:
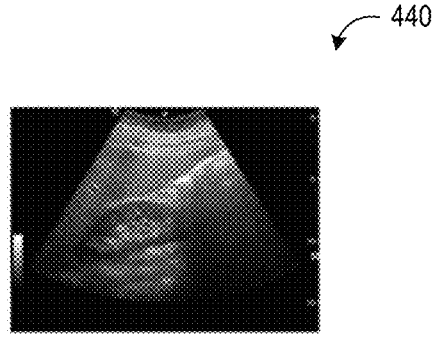
FIG. 4E is an example ultrasound image acquired in a fifth scan plane.

Referring to FIGS. 4A, 4B, 4C, 4D, and 4E, example ultrasound images are shown that are acquired from an anatomical neighborhood comprising the RUQ, including a right kidney of a patient, where each example ultrasound image of the example ultrasound images is acquired at a different scan plane. FIG. 4A shows a first ultrasound image 400 of the right kidney in a target scan plane. FIG. 4B shows a second ultrasound image 410 of the right kidney in a superior scan plane. FIG. 4C shows a third ultrasound image 420 of the right kidney in an inferior scan plane. FIG. 4D shows a fourth ultrasound image 430 of the right kidney in the target scan plane, but rotated in a counter-clockwise direction. FIG. 4E shows a fifth ultrasound image 440 of the right kidney in the target scan plane, but rotated in a clockwise direction. If a training dataset is generated for the anatomical neighborhood comprising the RUQ, the first ultrasound image may be used as a target image of one or more training pairs of the dataset, and the second, third, fourth, and fifth ultrasound images may be used as input images of the one or more training pairs.

Returning to method 500, at 508, method 500 includes creating a dataset of image pairs of the training input images. Each image pair may include an input image and a target image (e.g., the input image 372 and the target image 374 of FIG. 3). For example, if the first ultrasound image of FIG. 4A is selected as a target image, and the second, third, fourth, and fifth ultrasound images of FIGS. 4B, 4C, 4D, and 4E, respectively, are selected as input images, then four image pairs may be included in the dataset of image pairs: a first image pair including the second ultrasound image of FIG. 4B and the first ultrasound image of FIG. 4A; a second image pair including the third ultrasound image of FIG. 4C and the first ultrasound image of FIG. 4A; a third image pair including the fourth ultrasound image of FIG. 4D and the first ultrasound image of FIG. 4A; and a fourth image pair including the fourth ultrasound image of FIG. 4D and the first ultrasound image of FIG. 4A. In various embodiments, the dataset of image pairs may include image pairs with a same target image, as well as image pairs with different target images.

Further, in some embodiments, the input image and the target image of a first image pair may be interchanged to create a second image pair, where the input image of the second image pair is the target image of the first image pair, and the target image of the second image pair is the input image of the first image pair. In other words, as the scan plane displacement prediction network may be trained to predict a displacement between two images of an anatomical neighborhood, either image may be included as a target image of an image pair for training purposes. As a result, a size of the training dataset may be effectively doubled by including image pairs with target images and input images interchanged.

At 510, method 500 includes estimating a displacement between scan planes of each image pair in the image pair dataset. The input image may have been acquired at a first scan plane, while the target image may have been acquired at a second, different scan plane. The displacement may be a measurable difference between the first scan plane and the second scan plane, such as an estimated adjustment of a handheld imaging device to achieve a position of the second scan plane from a position of the first scan plane.

In other words, estimating the displacement may include estimating a theoretical movement of the handheld imaging device (e.g., a probe) from a first estimated position (and/or orientation) of the handheld imaging device to a second estimated position (and/or orientation) of the handheld imaging device, where the input image of the image pair is acquired at the first estimated position (e.g., at a scan plane corresponding to the first estimated position), and the target image of the image pair is acquired at the second estimated position (e.g., at a scan plane corresponding to the second estimated position). The movement may include a direction of the movement, where the handheld imaging device may be moved from the first position to the second position by moving the handheld device in the direction. The direction may be a linear direction in one or more of three dimensions, or a rotational direction in one or more of three degrees of freedom. In some embodiments, the movement may also include a distance of the movement, where achieving the second position from the first position may include moving the handheld device in the direction for the distance.

For example, a user may manipulate a probe (e.g., an ultrasound probe) to attempt to acquire an image at a desired (e.g., target) scan plane. A first image acquired by the user may be at a first scan plane, which may not be the desired scan plane. To achieve the desired scan plane, the user may adjust a position of the probe, where the adjustment made to the position represents a displacement between the first scan plane and the desired scan plane. Adjusting the position of the probe may include moving the probe in a linear direction on a surface of a skin of a subject, the linear direction along a length of the probe, or along a width of the probe, or along a combination of the length of the probe and the width of the probe. Adjusting the position of the probe may include moving the probe in a linear direction perpendicular to the surface of the skin of the subject, for example, by applying a greater or lesser amount of pressure on the probe. Adjusting the position of the probe may also include adjusting an orientation of the probe. The probe may be rotated in a rotational direction, where the rotational direction may be a clockwise direction, or a counterclockwise direction. An angle of the probe may be adjusted, to tilt the probe to a desired angle. The probe may also be angled or tilted about the length or width of the probe (rock/pitch and tilt), as an alternative to linear directional movement when fine movement is desired. In other words, in some circumstances, an up/down tilt of the probe may be adjusted as an alternative to a linear adjustment of a position of the probe in an up/down direction, and/or in other circumstances, a left/right pitch of the probe may be adjusted as an alternative to a linear adjustment of a position of the probe in a left/right direction.

Thus, the displacement between the first scan plane and the desired scan plane may include positional, rotational, and angular components, where the displacement may comprise a combination, summation, or selection of one or more of the positional, rotational, and angular components. For example, in a first embodiment, the displacement may be a positional displacement; in a second embodiment, the displacement may be a rotational displacement; in a third embodiment, the displacement may be a combination of the positional displacement and the rotational displacement; in a fourth embodiment, the displacement may be a summation of the positional displacement, the rotational displacement, and an angular displacement; and so on. In various embodiments, the displacement may be represented as a displacement vector, where different values of the displacement vector may represent different components of the displacement. A number of the different values of the displacement vector may correspond to a number of parameters of an output layer of the scan plane displacement prediction network, such that a value of a loss function calculated based on a difference between an output of the scan plane displacement prediction network and the displacement vector may be minimized.

How the displacement is measured, estimated, or represented may depend on a use of the displacement. In some embodiments where the displacement may be used to provide probe guidance to the user, a positional displacement may be used to display a guidance cue (e.g., an arrow, a different directional indicator, an icon, etc.) on a display device coupled to the probe indicating a suggested linear direction to move the probe, and/or a different guidance cue (e.g., a curved arrow, a different rotational indicator, an icon, etc.) to indicate a suggested rotational direction to rotate the probe. Use of the displacement to provide probe guidance is described in greater detail below in relation to FIG. 6. In other embodiments where the displacement may be used to assess a performance of the user during an examination (e.g., for training purposes), an assessment may be based on a summation, or weighted combination of the positional displacement, the rotational displacement, and the angular displacement. Use of the displacement to assess user performance is described in greater detail below in relation to FIG. 7.

In various embodiments, the theoretical movement of the handheld imaging device (e.g., a probe) from the first estimated position of the handheld imaging device to the second estimated position of the handheld imaging device may be estimated by an expert user of the handheld imaging device. In some embodiments, curation may be performed by the expert user in an offline mode (e.g., using recorded images), while in other embodiments, curation may be performed in an online mode (e.g., during a live scan).

At 512, method 500 includes creating a dataset of training pairs, each training pair including an input pair and a corresponding target estimated displacement of the input image pair, and method 500 ends.

Figure 6:
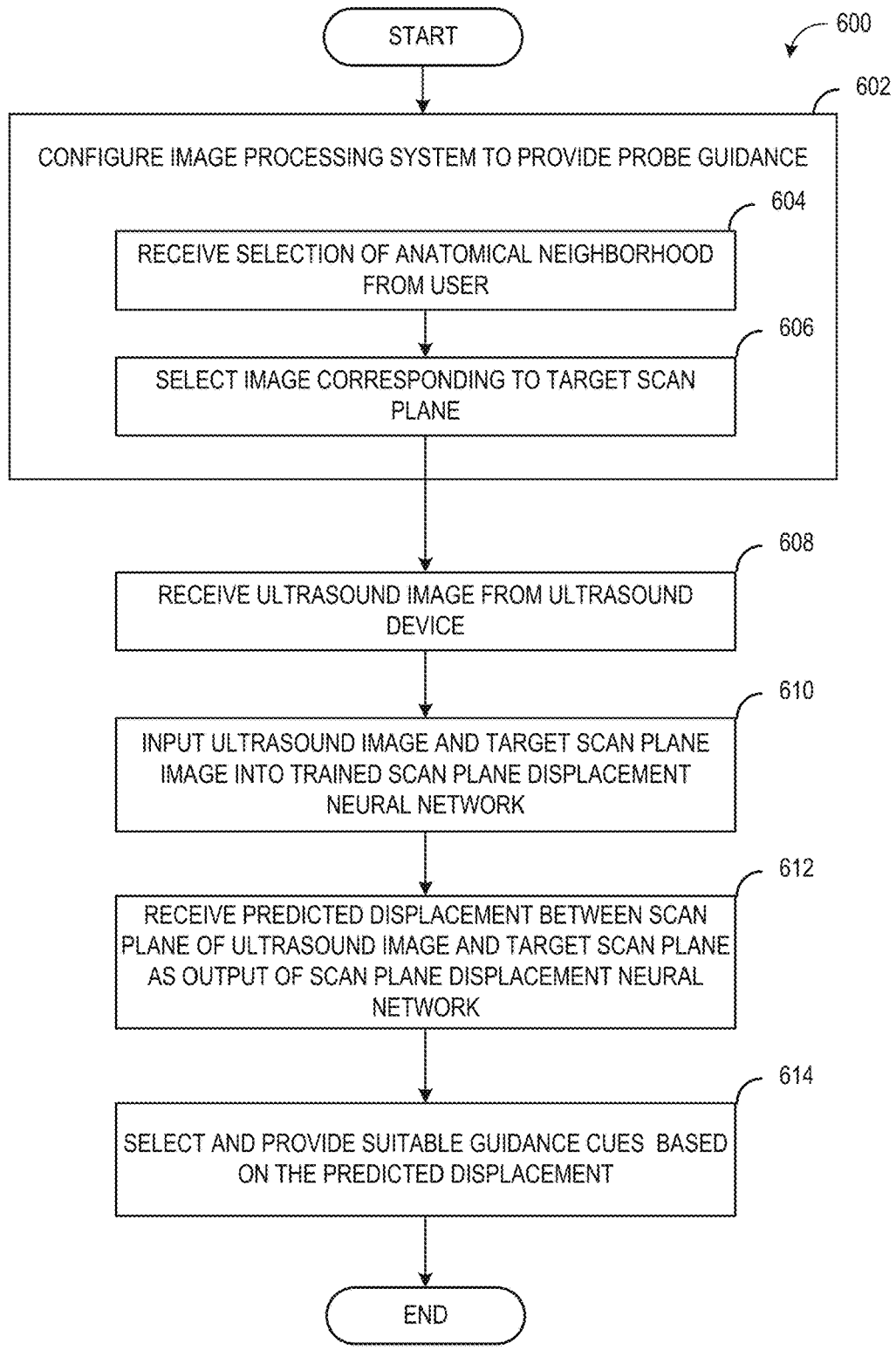
FIG. 6 is a flowchart illustrating an exemplary procedure for generating probe guidance cues on a display screen of an image processing system based on an output of a scan plane displacement prediction network.

Referring now to FIG. 6, an exemplary method 600 is shown for providing guidance information for an ultrasound probe based on an output of a trained scan plane displacement prediction network (e.g., scan plane displacement prediction network 302), where the output is a predicted displacement between a scan plane of new input image and a scan plane of a corresponding target image. One or more steps of method 600 may be carried out by an inference module of an image processing system, such as inference module 212 of image processing system 202 and/or inference module 396 of FIG. 3. Specifically, one or more instructions of method 600 may be executed by a processor of the image processing system (e.g., processor 204). It should be appreciated that while method 600 is described in reference to the ultrasound probe, in other embodiments, one or more steps of method 600 may be applied to a different type of probe or handheld imaging device, and/or a different type of medical image.

Method 600 begins at 602, where method 600 includes configuring the image processing system to provide probe guidance information to a user. At 604, configuring the image processing system to provide the probe guidance information to the user may include receiving from the user a selection of an anatomical neighborhood within which the probe guidance information will be generated. In some embodiments, the selection of the anatomical neighborhood may be automatically received when the user configures the image processing system to perform a certain type of examination. For example, when starting an ultrasound examination on a heart of a subject, the user may indicate via one or more settings of the image processing system that the ultrasound examination may be related to the heart of the subject. Based on the one or more settings of the image processing system indicating that the ultrasound examination may be related to the heart, an anatomical neighborhood of a heart may be automatically selected by the image processing system. In other embodiments, the user may select an anatomical neighborhood, for example, by manually adjusting a setting of the image processing system.

At 606, configuring the image processing system may include selecting an image corresponding to a target scan plane of the anatomical region. In some embodiments, the selection of the target scan plane image may be automatically determined when the user configures the image processing system to perform a certain type of examination. For example, if a certain type of ultrasound examination related to the heart of the subject is selected by the user, the image processing system may automatically select a suitable target scan plane image. In other embodiments, the user may manually select an image corresponding to a desired target scan plane. For example, the user may select a target scan plane image from a library of target scan plane images. The library of target scan plane images may be stored in a non-transitory memory of the image processing system (e.g., non-transitory memory 206), or the library of target scan plane images may be an external library electronically coupled to the image processing system.

At 608, method 600 includes receiving an ultrasound image from the ultrasound probe. The ultrasound image may be acquired by the ultrasound probe as the user manipulates the ultrasound probe on a body of a subject during the examination. As the user adjusts a position and/or orientation of the probe on the body of the subject, new ultrasound images may be generated and received in real time.

At 610, method 600 includes introducing the ultrasound image and the target scan plane image into the trained scan plane displacement neural network as input data. In various embodiments, inputting the ultrasound image and the target scan plane image into the trained scan plane displacement neural network may include converting the ultrasound image and the target scan plane image into arrays of pixel intensity values corresponding to pixels of the ultrasound image and the target scan plane image, and multiplying the pixel intensity values by parameters of an input layer of the trained scan plane displacement neural network. A result of multiplying the pixel intensity values by the parameters of the input layer may be propagated through the scan plane displacement neural network, to generate an output of the scan plane displacement neural network.

At 612, method 600 includes receiving a predicted displacement between a scan plane of the ultrasound image and the target scan plane as an output of the trained scan plane displacement neural network. As described above, the predicted displacement may include various components, such as a positional displacement component, a rotational displacement component, and/or an angular displacement component. In various embodiments, the predicted displacement may be received from the scan plane displacement neural network as a vector of parameter values, where each parameter value of the vector of parameter values is an output of a node of an output layer of the scan plane displacement neural network.

At 614, method 600 includes selecting and providing one or more suitable guidance cues (e.g., on a display screen of the image processing system such as display device 234 of image processing system 202, or via a speaker of the image processing system), based on the predicted displacement. For example, the predicted displacement may include a positional displacement component, such as a direction to move the ultrasound probe to achieve the target scan plane. Based on the direction, method 600 may include displaying a first probe guidance cue (e.g., an arrow, or similar visual element, indicating the direction) on the display screen, superimposed upon the ultrasound image, where the first probe guidance cue indicates the direction to move the ultrasound probe to achieve the target scan plane.

Additionally or alternatively, the predicted displacement may include a rotational displacement component, such as a rotational direction to rotate the ultrasound probe to achieve the target scan plane. Based on the rotational direction, method 600 may include displaying a second probe guidance cue (e.g., a curved arrow, or similar visual element, indicating a pitch, yaw and/or roll adjustment) on the display screen, superimposed upon the ultrasound image, where the second probe guidance cue may indicate the rotational direction to rotate the ultrasound probe to achieve the target scan plane. Additionally or alternatively, the predicted displacement may include an angular displacement component, such as an angular direction to tilt the ultrasound probe to achieve the target scan plane. Based on the angular direction, method 600 may include displaying a third probe guidance cue on the display screen to indicate the angular direction to tilt the ultrasound probe to achieve the target scan plane. In other embodiments, an audio probe guidance cue (e.g., verbal instructions, a sound, etc.) may be played to the user via a speaker coupled to the ultrasound probe and/or image processing system, instead of or in addition to displaying a visual guidance cue on the display screen. In this way, one or more different guidance cues may be provided to the user during the examination to provide robust probe guidance information in aiding the user in acquiring a suitable ultrasound image (e.g., at an appropriate scan plane), based on the predicted displacement received from the trained scan plane displacement neural network.

Figure 7:
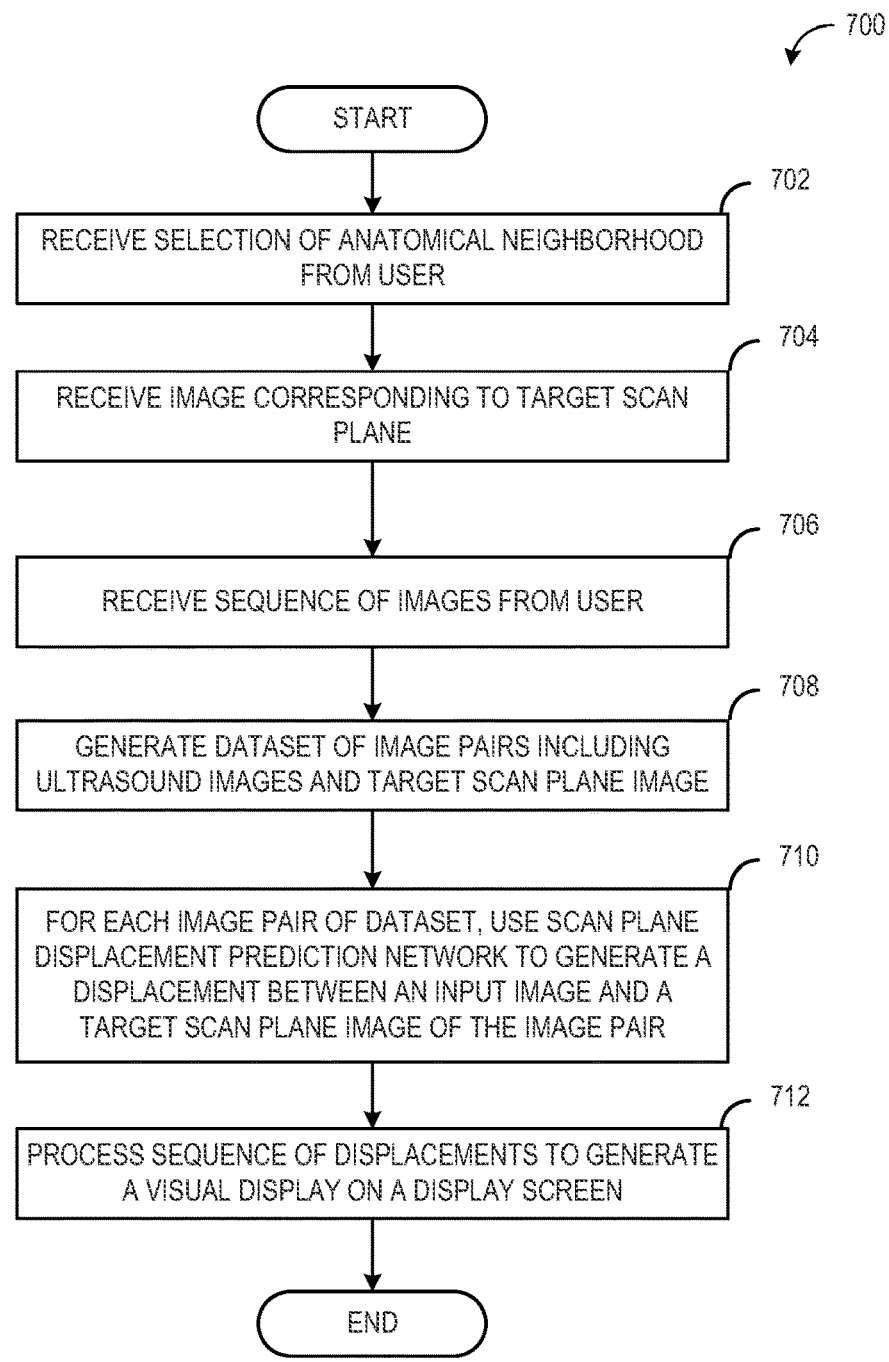
FIG. 7. is a flowchart illustrating an exemplary procedure for assessing a performance of an operator of a handheld imaging device in achieving a desired scan plane by predicting a scan plane displacement between images of a time sequence of images.

Referring now to FIG. 7, an exemplary method 700 is shown for providing an assessment of a performance of a user of a handheld imaging device (e.g., an ultrasound probe) based on an output of a trained scan plane displacement prediction network (e.g., scan plane displacement prediction network 302), where the output includes one or more predicted displacements between scan planes of a sequence of one or more input images and a scan plane of a corresponding target image. One or more steps of method 700 may be carried out by an inference module of an image processing system, such as inference module 212 of image processing system 202 and/or inference module 396 of FIG. 3. Specifically, one or more instructions of method 700 may be executed by a processor of the image processing system (e.g., processor 204).

Method 700 begins at 702, where method 700 includes receiving a selection of an anatomical neighborhood from the user. The user may select an anatomical neighborhood, for example, by manually adjusting a setting of the image processing system. In various embodiments, the user may open a training software application running on the image processing system with an intention of receiving feedback and/or information on the user's guidance of the handheld imaging device during an examination performed at a prior time. The feedback and/or information may include an assessment of a quality of the user's guidance, for example, in terms of how quickly and/or efficiently the user was able to achieve a target scan plane. The feedback and/or information may also include suggestions for achieving the target scan plane in a quicker or more efficient manner. When the user opens the training software application, the software application may prompt the user to select the anatomical neighborhood.

In other embodiments, the anatomical neighborhood may be automatically selected by the training software application and/or the image processing system in response to the user selecting a different setting of the training software application and/or the image processing system. For example, the user may select one or more images to analyze, and the training software application and/or the image processing system may select the anatomical neighborhood based on the one or more selected images.

At 704, method 700 includes receiving an image corresponding to a target scan plane of the anatomical region. As described above at 702 in reference to the anatomical neighborhood, the user may select the image corresponding to the target scan plane by manually adjusting a setting of the image processing system and/or the training software application. For example, as described above, the user may select the image corresponding to the target scan plane from a library of target scan plane images relevant to the anatomical neighborhood. In other embodiments, the user may load the image corresponding to the target scan plane from a memory of the image processing system (e.g., non-transitory memory 206 of FIG. 2), or from a separate file system electronically coupled to the image processing system, or from a location on a network (e.g., the Internet). It should be appreciated that while method 700 includes receiving the image corresponding to the target scan plane after receiving the selection of the anatomical neighborhood, in some embodiments, step 704 may performed before step 702, or one or more other steps of method 700 may be performed in a different order, without departing from the scope of this disclosure.

At 706, method 700 includes receiving a sequence of images from the user. The sequence of images may be a sequence of one or more image frames recorded during a prior examination. In one embodiment, the image processing system may record the sequence of one or more image frames of the prior examination, and allow the user to select and load the sequence via a user input device (e.g., user input device 232) of the image processing system. In other embodiments, the user may load the sequence of images from a different file or network location.

At 708, method 700 includes generating a dataset of image pairs including images from the sequence of images and the target scan plane image. Each image pair may include a consecutive input image of the sequence of images and the target scan plane image. For example, if the sequence of images includes 100 images, 100 image pairs may be generated. A first image pair may include a first consecutive image of the sequence of images and the target scan plane image; a second image pair may include a second consecutive image of the sequence of images and the target scan plane image; and so on.

At 710, method 700 includes, for each image pair of the dataset, using the trained scan plane displacement neural network to estimate a displacement between the consecutive input image of the image pair and the target scan plane image of the image pair (e.g., a displacement between a scan plane of the input image and the target scan plane), as described above in reference to method 600. By estimating the displacement for each image pair, a first sequence of scan plane displacements may be created, corresponding to the sequence of images. For example, the first sequence of scan plane displacements may include a first displacement between the first consecutive image and the target scan plane; a second displacement between the second consecutive image and the target scan plane; a third displacement between the third consecutive image and the target scan plane; and so on.

Alternatively, the trained scan plane displacement neural network may be used to estimate displacements between consecutive images of the sequence of images to generate a second sequence of scan plane displacements. For example, the trained scan plane displacement neural network may estimate a first displacement between a first input image of a first image pair and a second, consecutive input image of a second image pair; a second displacement between the second input image of the second image pair and a third, consecutive input image of a third image pair; and so on. The second sequence of scan plane displacements may provide for an alternate assessment of the performance of the user.

At 712, method 700 includes processing a sequence of displacements corresponding to the image pairs of the dataset to generate guidance information on a display screen of the image processing system (e.g., display device 234 of image processing system 202). The guidance information may aid the user in analyzing the performance of the user.

In some embodiments, the visual display may include a quality assessment of the performance, where the quality assessment is based at least partially on the sequence of displacements. For example, the quality assessment may be based on an efficiency of the user in navigating from an initial scan plane to the target scan plane, where the efficiency may be estimated as a function of the sequence of displacements (e.g., an average, or a summation of each scan plane displacement of the sequence of displacements). In some embodiments, the first sequence of scan plane displacements described above may be used to rate an ability of the user to make iterative adjustments to a position or orientation of the handheld imaging device towards achieving the target scan plane. In other embodiments, the second sequence of scan plane displacements described above may be used to rate a smoothness of a motion or change of orientation of the handheld imaging device in achieving the target scan plane. In still other embodiments, the first sequence of scan plane displacements and/or the second sequence of scan plane displacements may be used to assess the performance of the user in a different way.

In some embodiments, the visual display may include suggested alternative movements of the handheld imaging device, based at least partially on the sequence of displacements. The visual display may include one or more visual elements showing, for an input image of the sequence of images, a movement of the handheld imaging device to attempt to achieve the target scan plane, as well as a suggested movement that could have been made at the scan plane of the input image that may have led to achieving the target scan plane more rapidly or efficiently. As one example, when the input image is displayed on the display screen, the image processing system may display a first arrow in a first color indicating a direction in which the user adjusted the handheld imaging device, and a second arrow in a second color indicating a preferred or recommended direction to adjust the handheld imaging device. By visually comparing the first arrow to the second arrow on a plurality of input images of the sequence of images, the user may evaluate how well the user performed in the examination. Evaluating how well the user performed in the examination may include, for example, identifying any mistakes made, poor habits or tendencies, incidences of over-compensation or under-compensation for imprecise movements, difficulties identifying a direction to move in, and the like. In some embodiments, the user may view the sequence of images in real time, and the visual elements may be adjusted dynamically on the display screen in real time. In other embodiments, the user may be able to view individual input images and/or step forward and/or backward through the individual input images to monitor a sequence of actions in a step-by-step manner. In still other embodiments, other visual elements may be used or added. For example, a timer may be displayed on the screen to indicate a passage of time, or patient information of a subject of the examination (e.g., vital signs, vital signs of a fetus, etc.)

Thus, methods and systems are provided for predicting a displacement between a first scan plane and a second, target scan plane based on an output of a generic deep learning neural network model, and using the predicted displacement to provide guidance information to an operator of a different handheld imaging device. In some embodiments, the guidance information may include real time guidance information, such as one or more cues displayed on a display screen coupled to the handheld imaging device indicating a suggested direction of movement and/or change in an orientation of the handheld imaging device to achieve the second, target scan plane from the first scan plane. In other embodiments, the guidance information may include an assessment of a performance of a user of the handheld imaging device during prior training or a prior examination, where the performance may be evaluated and/or rated as a function of scan plane displacements between image frames of a sequence of images and/or between each image frame of the sequence of images and a target scan plane. If and/or where the scan plane displacements indicate that the user may have been struggling to achieve the target scan plane, suggested or recommended adjustments of the handheld imaging device may be displayed on the display screen, for example, superimposed on the sequence of images during playback.

Because the generic deep learning neural network model is trained on training pairs including two scan planes of an anatomical neighborhood and a ground truth scan plane displacement between the two scan planes, and does not rely on a presence of a specific anatomical feature, registration with an anatomical model, or expensive sensors (e.g., of an IMU), the generic deep learning neural network may subsequently be used to generate the guidance information for any target scan plane in the anatomical neighborhood. Thus, the present disclosure may represent a lower cost and more scalable alternative to other approaches to probe guidance.

The technical effect of training the generic deep learning neural network model to predict a scan plane displacement between a first image acquired at a first scan plane and a second, target image acquired at a target scan plane, is that guidance information may be displayed to a user of a handheld imaging device, including in real time, that may aid the user in achieving the target scan plane, thereby increasing an efficiency of the user at achieving quality images in a short amount of time.

The disclosure also provides support for a method for an image processing system, comprising: training a deep learning (DL) neural network on training pairs including a first medical image of an anatomical neighborhood and a second medical image of the anatomical neighborhood as input data, and a ground truth displacement between a first scan plane of the first medical image and a second scan plane of the second medical image as target data, using the trained DL neural network to predict a displacement between a first scan plane of a new medical image of the anatomical neighborhood and a target scan plane of a reference medical image of the anatomical neighborhood, and displaying guidance information for a handheld imaging device used to acquire the new medical image on a display screen of the image processing system based on the predicted displacement and/or storing the guidance information for further processing. In a first example of the method, the handheld imaging device is an ultrasound probe, and the guidance information is probe guidance information. In a second example of the method, optionally including the first example, the ground truth displacement used as target data is an estimated motion of the ultrasound probe from a first position and/or orientation where the first image is acquired to a second position and/or orientation where the second image is acquired, the estimated motion generated by an expert. In a third example of the method, optionally including one or both of the first and second examples, the probe guidance information is provided in real time. In a fourth example of the method, optionally including one or more or each of the first through third examples, the probe guidance information includes at least one of: a suggested up/down linear adjustment or up/down tilt adjustment of a position of the ultrasound probe along a width of a probe, a suggested left/right adjustment or left/right pitch adjustment of the ultrasound probe along a length of the probe, and a suggested rotational adjustment of the ultrasound probe. In a fifth example of the method, optionally including one or more or each of the first through fourth examples, the suggested rotational adjustment includes a suggested adjustment to a roll of the ultrasound probe. In a sixth example of the method, optionally including one or more or each of the first through fifth examples, the probe guidance information includes at least one of a visual guidance cue displayed on a display device coupled to the ultrasound probe and an audio feedback played on a speaker coupled to the ultrasound probe. In a seventh example of the method, optionally including one or more or each of the first through sixth examples, the probe guidance information includes an assessment of a performance of a user of the image processing system in achieving a target scan plane during an examination. In a eighth example of the method, optionally including one or more or each of the first through seventh examples, the target scan plane is selected by a user of the image processing system based on at least one of the anatomical neighborhood and a type of examination. In a ninth example of the method, optionally including one or more or each of the first through eighth examples, the target scan plane is predicted by the image processing system based on at least one of the anatomical neighborhood, a type of examination, and a motion of an ultrasound probe. In a tenth example of the method, optionally including one or more or each of the first through ninth examples, the first medical image is acquired at a first scan depth, and the second medical image is acquired at a second scan depth, the second scan depth different from the first scan depth, further comprising: prior to training the DL neural network, pre-processing the first medical image and the second medical image to match a space between pixels or voxels of the first medical image and a space between pixels or voxels of the second medical image.

The disclosure also provides support for an image processing system comprising: a processor, and a non-transitory memory including instructions that when executed cause the processor to: predict a displacement between a first scan plane of a medical image of an anatomical neighborhood acquired via a probe and a second, target scan plane of the anatomical neighborhood, using a trained scan plane displacement prediction network, the scan plane displacement prediction network trained on a dataset of training pairs, each training pair including: a first medical image of the anatomical neighborhood and a second medical image of the anatomical neighborhood as input data, and a displacement between a scan plane of the first medical image and a scan plane of the second medical image as ground truth target data, and based on the predicted displacement, display probe guidance information to a user of the image processing system via a display device communicably coupled to the image processing system and/or store the probe guidance information in a storage device communicably coupled to the image processing system. In a first example of the system: the predicted displacement is not based on one or more sensors of an inertial measurement unit (IMU), and the predicted displacement is not based on identifying or detecting a position of a feature of the anatomical neighborhood. In a second example of the system, optionally including the first example, the probe guidance information includes a suggested movement of the probe to achieve the second, target scan plane from the first scan plane. In a third example of the system, optionally including one or both of the first and second examples, the suggested movement includes both an adjustment to a position of the probe and an adjustment to an orientation of the probe. In a fourth example of the system, optionally including one or more or each of the first through third examples, the first medical image immediately precedes the second medical image in a sequence of image frames, and the probe guidance information includes an assessment of a movement of the probe from the first scan plane towards the second, target scan plane. In a fifth example of the system, optionally including one or more or each of the first through fourth examples, the training pairs include a first set of training pairs where the first medical image and the second medical image are acquired using a same set of scan parameters, and a second set of training pairs where the first medical image and the second medical image are acquired using one or more different scan parameters. In a sixth example of the system, optionally including one or more or each of the first through fifth examples, the probe is an ultrasound probe.

The disclosure also provides support for a method for an image processing system, comprising: recording a time sequence of medical images acquired by a user of a handheld medical imaging device during an examination of a subject, determining a scan plane of each medical image of the time sequence of medical images, to generate a time sequence of scan planes, using a trained scan plane displacement prediction network to calculate a displacement between each scan plane of the time sequence of scan planes and an immediately preceding and/or immediately following scan plane, to generate a time sequence of scan plane displacements, and based on the time sequence of scan plane displacements, display an assessment of one or more manipulations of the handheld medical imaging device performed by the user of the handheld medical imaging device during the examination on a display device of the image processing system. In a first example of the method, the assessment includes providing one or more suggested alternative manipulations to the one or more manipulations of the handheld medical imaging device performed by the user.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method for an image processing system, comprising:
    training a deep learning (DL) neural network on training pairs including a first medical image of an anatomical neighborhood and a second medical image of the anatomical neighborhood as input data, and a ground truth displacement between a first scan plane of the first medical image and a second scan plane of the second medical image as target data;
    using the trained DL neural network to predict a displacement between a first scan plane of a new medical image of the anatomical neighborhood and a target scan plane of a reference medical image of the anatomical neighborhood; and
    displaying guidance information for a handheld imaging device used to acquire the new medical image on a display screen of the image processing system based on the predicted displacement and/or storing the guidance information for further processing.

2. The method of claim 1, wherein the handheld imaging device is an ultrasound probe, and the guidance information is probe guidance information.

3. The method of claim 2, wherein the ground truth displacement used as target data is an estimated motion of the ultrasound probe from a first position and/or orientation where the first image is acquired to a second position and/or orientation where the second image is acquired, the estimated motion generated by an expert.

4. The method of claim 2, wherein the probe guidance information is provided in real time.

5. The method of claim 4, wherein the probe guidance information includes at least one of:
    a suggested up/down linear adjustment or up/down tilt adjustment of a position of the ultrasound probe along a width of a probe;
    a suggested left/right adjustment or left/right pitch adjustment of the ultrasound probe along a length of the probe; and
    a suggested rotational adjustment of the ultrasound probe.

6. The method of claim 5, wherein the suggested rotational adjustment includes a suggested adjustment to a roll of the ultrasound probe.

7. The method of claim 5, wherein the probe guidance information includes at least one of a visual guidance cue displayed on a display device coupled to the ultrasound probe and an audio feedback played on a speaker coupled to the ultrasound probe.

8. The method of claim 2, wherein the probe guidance information includes an assessment of a performance of a user of the image processing system in achieving a target scan plane during an examination.

9. The method of claim 1, wherein the target scan plane is selected by a user of the image processing system based on at least one of the anatomical neighborhood and a type of examination.

10. The method of claim 1, wherein the target scan plane is predicted by the image processing system based on at least one of the anatomical neighborhood, a type of examination, and a motion of an ultrasound probe.

11. The method of claim 1, wherein the first medical image is acquired at a first scan depth, and the second medical image is acquired at a second scan depth, the second scan depth different from the first scan depth, further comprising:
prior to training the DL neural network, pre-processing the first medical image and the second medical image to match a space between pixels or voxels of the first medical image and a space between pixels or voxels of the second medical image.

12. An image processing system comprising:
a processor, and a non-transitory memory including instructions that when executed cause the processor to:
predict a displacement between a first scan plane of a medical image of an anatomical neighborhood acquired via a probe and a second, target scan plane of the anatomical neighborhood, using a trained scan plane displacement prediction network, the scan plane displacement prediction network trained on a dataset of training pairs, each training pair including:
a first medical image of the anatomical neighborhood and a second medical image of the anatomical neighborhood as input data, and
a displacement between a scan plane of the first medical image and a scan plane of the second medical image as ground truth target data; and
based on the predicted displacement, display probe guidance information to a user of the image processing system via a display device communicably coupled to the image processing system and/or store the probe guidance information in a storage device communicably coupled to the image processing system.

13. The image processing system of claim 12, wherein:
the predicted displacement is not based on one or more sensors of an inertial measurement unit (IMU); and
the predicted displacement is not based on identifying or detecting a position of a feature of the anatomical neighborhood.

14. The image processing system of claim 12, wherein the probe guidance information includes a suggested movement of the probe to achieve the second, target scan plane from the first scan plane.

15. The image processing system of claim 14, wherein the suggested movement includes both an adjustment to a position of the probe and an adjustment to an orientation of the probe.

16. The image processing system of claim 12, wherein the first medical image immediately precedes the second medical image in a sequence of image frames, and the probe guidance information includes an assessment of a movement of the probe from the first scan plane towards the second, target scan plane.

17. The image processing system of claim 12, wherein the training pairs include a first set of training pairs where the first medical image and the second medical image are acquired using a same set of scan parameters, and a second set of training pairs where the first medical image and the second medical image are acquired using one or more different scan parameters.

18. The image processing system of claim 12, wherein the probe is an ultrasound probe.

19. A method for an image processing system, comprising:
recording a time sequence of medical images acquired by a user of a handheld medical imaging device during an examination of a subject;
determining a scan plane of each medical image of the time sequence of medical images, to generate a time sequence of scan planes;
using a trained scan plane displacement prediction network to calculate a displacement between each scan plane of the time sequence of scan planes and an immediately preceding and/or immediately following scan plane, to generate a time sequence of scan plane displacements; and
based on the time sequence of scan plane displacements, display an assessment of one or more manipulations of the handheld medical imaging device performed by the user of the handheld medical imaging device during the examination on a display device of the image processing system.

20. The method of claim 19, wherein the assessment includes providing one or more suggested alternative manipulations to the one or more manipulations of the handheld medical imaging device performed by the user.

* * * * *